| United States Patent [19] | [11] | 4,384,992 |
| Capron et al. | [45] | May 24, 1983 |

[54] **NOVEL PEPTIDE FROM CULTURES OF *SCHISTOSOMA MANSONI*, A PROCESS FOR PRODUCING IT AND PHARMACEUTICAL COMPOSITIONS CONTAINING THE SAME**

[76] Inventors: André Capron, 58, rue du Capitaine Jasmin, 59133 Phalempin; Christine Mazingue, Appt 3 Res Amdia III, Rue Jardin de l'Arc, 59110 La M nadeleine; Daniel Camus, 1 Allée Chantecler, 59650 Villeneuve D'Ascq, all of France

[21] Appl. No.: 228,994

[22] Filed: Jan. 27, 1981

[51] Int. Cl.³ .............................................. C07G 7/00
[52] U.S. Cl. .............................. 260/112 R; 424/177; 435/68
[58] Field of Search ..................... 260/112 R; 435/68; 424/123, 177

[56] References Cited

FOREIGN PATENT DOCUMENTS 2447194 8/1980 France ........................... 260/112 R

OTHER PUBLICATIONS

Chem. Abs. 91:154657k.
Chem. Abs. 84:28265y.
Chem. Abs. 82:2561a.

*Primary Examiner*—Allan Lieberman
*Assistant Examiner*—Patricia Short
*Attorney, Agent, or Firm*—Omri M. Behr

[57] ABSTRACT

A small peptide obtained from *Schistosoma mansoni* has a molecular weight between 500 and 1000. It is water soluble. It is heat-stable. It inhibits the mast cell degranulation in vitro and in vivo elicited by chemical compounds or anaphylactic reactions. It prevents passive or active cutaneous anaphylactic reactions.

5 Claims, No Drawings

NOVEL PEPTIDE FROM CULTURES OF *SCHISTOSOMA MANSONI*, A PROCESS FOR PRODUCING IT AND PHARMACEUTICAL COMPOSITIONS CONTAINING THE SAME

PRIOR ART

The prior art may be illustrated with the following references: B. M. Ogilvie and V. E. Jones—Progress in Allergy 17 (1973) 93 A. Capron and cowork.—Path. Biol. 16 (1968) 121 J. P. Dessaint and cowork.—Europ J. Immunol. 7 (1977) 624 C. Mazingue—Int. archives Allergy Appl. Immuno 63 (1980) 178

SUMMARY OF THE INVENTION

The peptide of small molecular weight obtained from *Schistosoma mansoni* appears dialysable, heat resistant and soluble in trichloracetic acid. It prevents or inhibits the mast cell degranulation in vitro and in vivo, induced by chemical compounds or anaphylactic reactions.

Therefore, it inhibits the serotonin release from the mast cells induced by compound 48/80 or Polymyxin B or by an anaphylactic system, by mere incubation.

This peptide may be formulated into pharmaceutical compositions in conjunction or admixture with an inert non-toxic acceptable pharmaceutical carrier or vehicle. It may be used for treating or preventing conditions correlated to allergy, anaphylaxia and migraine.

PREFERRED EMBODIMENTS

This invention relates to a polypeptide of low molecular weight obtained from the cultures of adults *Schistosoma mansoni*.

This peptide shows the particular reactions of the peptides. It is not retained by a diafiltration membrane such as the membrane of reticulated dextran sold under the tradename AMICON X 100 which is devised to retain the polypeptide having a molecular weight higher than 1000. The determinations of molecular weight performed using physical methods (centrifugation, electrophorese), or chemical methods seem to indicate that the molecular weight lies between 500 and 1000 and more likely closer to 500 than 1000.

It is thermostable, soluble in trichloracetic acid and in water.

This invention also relates to a process for producing the afore-defined peptide, consisting in incubating for a fixed set of time adults schistosomes in a saline solution then separately the insoluble bodies of the trematods by ultra-filtration, recovering the clear filtrate, dialysing the latter against distilled water, separating the dialysate and lyophilisine it.

The polypeptide thus obtained is a colourless powder, soluble in water and in saline.

According to a more specific procedure, the process for producing the polypeptide of the invention, the ultra-filtration is carried out using a membrane sold under the tradename MILLIPORE having a mean diameter of the pores of about 0.22 m$\mu$, the dialysis is carried out using a cell fitted with a membrane AMICON X 100 and the first incubation lasts for 3 hours.

The polypeptide of this invention is endowed with very useful pharmacological properties. It is able to inhibit "in vitro" and "in vivo" the mast cell degranulation elicited by chemical compounds or anaphylactic reactions.

Namely serotonin release normally induced by the chemical compounds such as compound 48/80, Polymyxin B or by an anaphylactic system (ovalbumin-antiovalbumin) was inhibited when mast cells were previously incubated with the polypeptide from *Schistosoma mansoni*.

Cutaneous anaphylactic reactions elicited by the compound 48/80 or polymyxin B and passive or active cutaneous anaphylactic reactions, were inhibited by the injection of the polypeptide prior the challenge.

The anaphylactic shock evoked by ovalbumin was also inhibited in guinea pigs by a previous injection of the polypeptide, preferably by intraperitoneal way.

These effects appear to be specific whilst the polypeptide has no action either on the eosinophils or the mast cell mediators. No effect of the polypeptide was observed on the growth of HeLa cells or of the J.111 human monocytic cell line.

The increase of intracellular cyclic AMP levels suggests that modulation of cyclic AMP is involved on the mechanism of inhibition. The polypeptide from schistosoma also inhibits the mast cell-dependant eosinophil cytotoxicity for schistosomuls sensitized with IgG2a antibodies.

This polypeptide is distinct of the circulating M antigen (TCA soluble, thermostable) previously described and purified from schistosomes. This factor has no inhibitory action against cutaneous allergy and very likely possesses a high molecular weight.

This invention also relates to pharmaceutical compositions containing as active ingredient the polypeptide from schistosoma in conjunction or admixture with one or more non toxic, inert, pharmaceutically-acceptable carriers or vehicles. In a preferred way, the carrier or vehicle will be selected among those suitable for parenteral administration, permucous administration, percutaneous administration, rectal way or perlingual way of administration.

Appropriate pharmaceutical compositions are, for example, injectable solutions or suspensions packed in ampouls, phials, multi-doses flasks, auto-injectable syringes, sublingual tablets, suppositories, pressurized solutions for permucous way of administration, solutions or suspensions in a polar solvent for percutaneous application.

The usual dosology may broadly vary. It depends namely of the therapeutic use and the condition of the patient. Due to the very low toxicity of the polypeptide from schistosoma, the dosology may be very significantly increased when a more intensive effect is desired.

This invention also relates to a method for preventing or treating allergic states or migraine caused by the "in vivo" degranulation of the mastocystes, which consists in administering to the humans suffering from said conditions, a safe but efficient amount of the afore-defined polypeptide from schistosoma.

The following examples are merely intended to illustrate the invention without restricting it in any manner.

EXAMPLE I

Preparation of the polypeptide from *Schistosoma mansoni*

10,000 adult schistosomas recovered from 40 days infected hamsters, were incubated for 3 hours in 10 ml 5°/$_{oo}$ sodium chloride solution.

The incubation solution was filtered on 0.22 $\mu$m Millipore membrane and the clear filtrate was dialysed against 10 ml distilled water. The dialysed solution was further lyophilysed.

The resulting powder was re-suspended in 1 ml saline for each testing.

EXAMPLE II

Pharmacological study of the polypeptide (a) Inhibition of mast cell-dependent eosinophil cytotoxicity by the polypeptide.

The eosinophil cytotoxicity for antibody sensitized *S. mansoni* schistosomuls requires the presence of a threshold number of mast cells. The possible inhibitory role of the polypeptide was investigated in that system. The results obtained show that the polypeptide significantly inhibited (76%) the cytotoxicity by a mixed population of eosinophils and mast cells. A significant inhibition was also obtained when intact purified mast cells were added to the mast cell-depleted population (48% inhibition, $P<0.05$). When the eosinophils were activated by the supernatant of degranulated mast cells, no inhibition was obtained in the presence of the polypeptide. These results indicated that the polypeptide does not interfere with the eosinophil counterpart but inhibits intact mast cells only.

(b) Effect of washing the cells on the inhibitory activity of the polypeptide

Labeled mast cells were preincubated at 37° C. for 30 min. with 10 $\mu$l of the polypeptide. The mast cells were washed three times and resuspended in culture medium. Degranulation was then induced either by polymyxin B or by the ovalbumin-antivalbumin system. Results obtained show the persistance of the inhibitory effect of the polypeptide on mast degranulation after washing.

(c) PCA reactions.

This test performed according to the techniques of OVARY. Accordingly antiovalbumin serum (0.1 ml) or *S. mansoni*—infected rat serum was injected intradermally into male Wistar rats. Forty-eight hours later, PCA reactions were elicited by the injection into the penis dorsal vein of 4 mg Evans blue together with 5 mg ovalbumin or 2 mg *S. mansoni* antigen respectively in 1 ml saline. The rats were killed 30 min. later and the areas of Evans blue diffusion on the internal face of the skin were measured with a planimeter.

(d) Active cutaneous anaphylactic reactions (ACA)

Wistar rats were immunized by intraperitoneal injection of 10 $\mu$g ovalbumin together with $5 \times 10^9$ *Bordetella pertussis*. Thirty days later, ACA reactions were induced by intradermal injection of 1 $\mu$g ovalbumin in 0.1 ml saline. Simultaneously, 4 mg Evans blue in 1 ml saline was administered intravenously. The rats were killed 30 min. later to examine the internal face of their skins as carried out for the PCA reactions.

The polypeptide from *Schistosoma mansoni* has been tested on PCA, ACA and cutaneous reactions induced by compound 48/80 or Polymyxin B. Skin reactions elicited by the compound 48/80 or Polymyxin B were inhibited by prior intradermal injection of 0.1 ml of the polypeptide into the same site. The ACA reactions to ovalbumin were significantly inhibited by 0.1 ml of the polypeptide but not physiological saline injected 15 min. before into the site of the challenge injection. The PCA reactions were markedly inhibited when 0.1 ml of the polypeptide was injected intradermally into the site of injection of the antiovalbumin or anti-*S. mansoni* antiserum, 15 min. before the intravenous injection of ovalbumin of *S. mansoni* antigen respectively. No inhibition was observed when physiological saline was injected instead of the polypeptide. Various doses of the polypeptide were injected 15 min. before the antigen challenge: undiluted or diluted ½ polypeptide inhibited the PCA reaction but no significant inhibition was obtained with higher dilutions. When the polypeptide was injected 48 hours before the injection of the antigen, no inhibition of the PCA reaction was observed. However, when the polypeptide was injected 3 hours or 30 min. before the ovalbumin, a marked inhibition of the PCA reaction was obtained. The intradermal injection of the polypeptide carried out simultaneously with intravenous injection of the antigen did not inhibit the PCA reaction.

(e) Anaphylactic shock in guinea pigs.

Guinea pigs (Janvier Strain) were immunized by intraperitoneal injection of 1 $\mu$g ovalbumin together with $5 \times 10^9$ *Bordetella pertussis*. The anaphylactic shock was elicited 2 months later by intraperitoneal injection of 1 mg ovalbumin. Thirty minutes prior to this injection, 3 ml saline or the polypeptide in saline were injected intraperitoneally.

The experiments have shown that the intraperitoneal injection of 1 mg ovalbumin into guinea pigs sensitized to ovalbumin induced tremor, dyspnea and death 30 min. to 2.5 hours later. When 3 ml of the polypeptide in physiological saline were injected intraperitoneally before the challenge, death did not occur and only an urinary emission was observed. Control injection of 3 ml of physiological saline did not inhibit the shock.

(f) [$^3$H] serotonin release assay.

This was carried out as previously described in the litterature. Peritoneal cells from Wister rats were incubated with (G-$^3$H) 5-hydroxytryptamine creatinine sulfate (10 Ci/mmole) at a dose of 2 $\mu$Ci/$10^6$/mast cells. The assay was performed in microtiter plates (Linbro. Flow Lab, Scotland). Mast cell degranulation was induced either by chemical compounds or by an antigen-antibody reaction. Fifty micro-liters of Polymyxin B sulfate (5 $\mu$g) or of the compound 48/80 (0.5 $\mu$g) were added to 50 $\mu$l of the cell suspension ($5 \times 10^4$ mast cells) together with 50 $\mu$l of Eagle's Minimum Essential Medium (MEM) (Institut Pasteur Production, Paris).

The cells were incubated 15 min. at 37° C., then centrifuged at $1,000 \times g$ for 10 min. Fifty microliters of the supernatant were transferred to counting vials. Treatment of cells with 50 $\mu$l of digestin (Merck, Darmstadt, R.F.A.) was used to measure the amount of serotonin releasable by mast cells. Ten milliliters of butyl-PPD (7 g/l) in toluene-triton (1/1) scintillation fluid were added to the counting vials (Block, Paris). Radioactivity was measured in a liquid scintillation counter (Nuclear Chicago, Ill).

For the antigen-anaphylactic antibody reaction, 50 $\mu$l of the undiluted anti-ovalbumin serum was added to 50 $\mu$l of the cell suspension. Passive sensitization of mast cells was achieved by incubation for 15 min. at 37° C.

The activity of the polypeptide has been tested on rat mast cells in vitro sensitized with 50 $\mu$l of undiluted antiovalbumin antiserum and incubated further with 50 $\mu$l ovalbumin. The preincubation of mast cells with 10 to 30 $\mu$l of the polypeptide 30 min. before the sensitization, significantly inhibited $^3$H serotonin release by ovalbumin. No significant release was induced by the polypeptide added to unsensitized mast cells. The activity of the polypeptide was also tested on mast cell degranulation induced by the compound 48/80 and Polymyxin B. The serotonin release normally induced by these chemical compounds was inhibited by preincubation of the mast cells with 10 or 20 $\mu$l of the polypeptide. The activity of the polypeptide was also assayed after heating the fraction 1 hour at 100° C. The mast cells were incubated 30 min. respectively with 10 μl of unheated polypeptide before degranulation induced by ovalbumin-antiovalbumin. Similar inhibitions were observed with the untreated and heated compound (46 and 48% respectively). Therefore, it may be assumed that it is perfectly thermostable.

(g) Effect of the polypeptide on cAMP levels in mast cells.

As mast cell degranulation is associated with the decrease of the levels of intracellular cyclic AMP, the activity of the polypeptide on intracellular AMP levels was investigated.

Mast cells were purified by centrifugation of rat peritoneal cells through 38% bovine serumalbumin. Purified mast cells ($1 \times 10^5$) were incubated 5 min. with 20 μl of the polypeptide. The cells were lysed by 50 μl 0.5 N sodium hydroxyde, neutralized with 50 μl 0.5 N perchloric acid and then boiled for 5 min. at 100° C. AMP was measured using the Becton-Dickinson radioimmunoassay kit. The results are expressed in picomoles per million cells (pmoles/$10^6$ cells).

From four different experiments, it was observed that AMP levels in unstimulated mast cells was $4.74 \pm 1.75$ pmoles/$10^6$ cells and was $458\% \pm 124$ increased after 5 min. incubation with the polypeptide. No measurable AMP was found in the polypeptide alone.

(h) Effect of the polypeptide on Hela and human monocytic cells.

The polypeptide has been shown to inhibit the proliferation of normal lymphocytes in vitro induced by mitogens or in mixed lymphocyte culture as well as the proliferation of 14 day-*S. mansoni* infected rat lymphocytes induced by *S. mansoni* antigen. Although the identity of the factors that inhibit lymphocyte proliferation and mast cell degranulation remains to be demonstrated, it was important to investigate the activity of the polypeptide from *S. mansoni* on other cells from various origins. The effect of the polypeptide (10 μl) was tested on $5 \times 10^5$ Hela cells or $2.5 \times 10^5$ (J.111) human monocytic cells. The count of viable cells 3 to 72 hours after the addition of the polypeptide showed only a slight and transient effect on cell viability and proliferation. The technique used was the following:

Hela cells (ATCC CCL 2.2) and human monocytic cell lines J.111 (ATCC CCL 24) were used as target cells. Cells were cultured in Petri dishes (Nunclon, Denmark) with Eagle's MEM supplemented with 15% heat-inactivited foetal calf serum together with 10 μl of the polypeptide. Viable cells were counted using the trypan blue exclusion technique.

What we claim is:

1. A process for purifying an antianaphylactically active polypeptide having a molecular weight of 500 to 1,000, being thermo stable and being soluble in water and in trichloracetic acid, derived from *Schistosoma Mansoni* which comprises the steps of:

incubating adult *S. Mansoni* organisms in a saline broth, thereafter subjecting said broth to filtration through an ultrafiltration membrane and retaining the filtrate, dialyzing said filtrate against distilled water in a dialysis cell provided with a membrane of reticulated dextran, said membrane being capable of blocking the passage therethrough of molecules having molecule weight greater than 1000, and retaining the diffusate from said dialysis.

2. A process in accordance with claim 1 additionally comprising the steps of removing water from the diffusate.

3. A process in accordance with claim 2 wherein the the removal step comprises lyophilization.

4. A process in accordance with claim 1 wherein the reticulated dextran membrane is an Amicon X-100 membrane.

5. A polypeptide produced in accordance with claim 1, having a molecular weight of 500 to 1000, being thermo stable and being soluble in water and in trichloracetic acid.

* * * * *